US007015294B2

(12) United States Patent
Dausch et al.

(10) Patent No.: US 7,015,294 B2
(45) Date of Patent: Mar. 21, 2006

(54) ACRYLATE POLYMERS BASED ON TERT-BUTYL ACRYLATE AND/OR TERT-BUTYL METHACRYLATE

(75) Inventors: Wilma M. Dausch, Limburgerhof (DE); Katrin Zeitz, Ludwigshafen (DE); Tanja Schneider, Bensheim (DE); Maximilian Angel, Schifferstadt (DE); Bernd de Potzolli, Bad Dürkheim (DE); Claudia Wood, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 302 days.

(21) Appl. No.: 10/399,498

(22) PCT Filed: Nov. 9, 2001

(86) PCT No.: PCT/EP01/12976

§ 371 (c)(1),
(2), (4) Date: Apr. 17, 2003

(87) PCT Pub. No.: WO02/38638

PCT Pub. Date: May 16, 2002

(65) Prior Publication Data

US 2004/0042994 A1    Mar. 4, 2004

(30) Foreign Application Priority Data

Nov. 10, 2000  (DE)  ................................ 100 55 776

(51) Int. Cl.
*C08F 116/14*    (2006.01)
(52) U.S. Cl. ................ 526/319; 526/328.5; 526/329.5; 526/329.7
(58) Field of Classification Search ................ 526/319, 526/328.5, 329.5, 329.7
See application file for complete search history.

(56) References Cited

U.S. PATENT DOCUMENTS 5,306,484 A    4/1994    Potthoff-Karl

FOREIGN PATENT DOCUMENTS

| DE | 199 08 183 | | 8/2000 |
|---|---|---|---|
| EP | 0 103 146 A1 | * | 3/1984 |
| EP | 696 916 | | 2/1996 |
| WO | 00/50480 | | 8/2000 |
| WO | 00/64983 | | 11/2000 |

* cited by examiner

Primary Examiner—Robert D. Harlan
(74) Attorney, Agent, or Firm—Novak Druce Deluca & Quigg, LLP; Jason D. Voight

(57) ABSTRACT

The invention relates to acrylate polymers comprising a K-value ranging from 10 to 60, which can be obtained by the radical polymerization of: 30 to 99 wt. % of tert-butyl acrylate and/or tert-butyl methacrylate designated as monomer A; 1 to 28 wt. % of acrylic acid and/or methacrylic acid designated as monomer B, and; 0 to 60 wt. % of a radically copolymerizable monomer or of a radically copolymerizable monomer mixture designated as monomer C, whereby at least one of monomers C yields a homopolymer with a glass-transition temperature lower than 30° C., with the provision that the wt. %'s total 100. The radical polymerization is carried out in the presence of alkane thiols with a C chain length of C 14 to C 22. The invention also relates to acrylate polymers comprising a K-value ranging from 10 to 60, which can be obtained by the radical polymerization of: 30 to 99 wt. % of tert-butyl acrylate and/or tert-butyl methacrylate designated as monomer A; 1 to 28 wt. % of acrylic acid and/or methacrylic acid designated as monomer B, and; 0 to 60 wt. % of a radically copolymerizable monomer or of a radically copolymerizable monomer mixture designated as monomer C, whereby at least one of monomers C yields a homopolymer with a glass-transition temperature lower than 30° C., with the provision that the wt. %'s total 100. The radical polymerization is carried out in the presence of alkane thiols with a C chain length of C 10 to C 22 followed by a hydrogen peroxide treatment. The invention also relates to the use of these acrylate polymers as film formers as well as to their use in cosmetic preparations.

14 Claims, No Drawings

ACRYLATE POLYMERS BASED ON TERT-BUTYL ACRYLATE AND/OR TERT-BUTYL METHACRYLATE

The present invention relates to novel polymers based on tert-butyl acrylate and/or tert-butyl methacrylate, to process for their preparation and also to their use, in particular in cosmetic preparations.

EP 379 082 A1 discloses copolymers based on tert-butyl acrylate and/or tert-butyl methacrylate with a K value of from 10 to 50 which are obtainable by free-radical polymerization of A) 75 to 99% by weight of tert-butyl acrylate and/or tert-butyl methacrylate,
B) 1 to 25% by weight of acrylic acid and/or methacrylic acid and
C) 0 to 10% by weight of a further free-radically copolymerizable monomer, where the carboxyl groups of the copolymer are not neutralized, partially neutralized or completely neutralized by amines.

EP 696 916 B1 discloses copolymers based on tert-butyl acrylate or tert-butyl methacrylate with a K value of from 10 to 50 which are obtainable by free-radical polymerization of A) 30 to 72% by weight of tert-butyl acrylate or tert-butyl methacrylate and a mixture thereof as monomer A,
B) 10 to 28% by weight of acrylic acid or methacrylic acid or a mixture thereof as monomer B and
C) 0 to 60% by weight of a free-radically copolymerizable monomer or a free-radically copolymerizable monomer mixture as monomer C, or at least one of the monomers C produces a homopolymer with a glass transition temperature of less than 30° C., where the carboxyl group of the copolymers are not neutralized, partially neutralized or completely neutralized.

The polymers described are suitable as film formers in cosmetic compositions. A disadvantage of the known polymers is primarily their strong intrinsic odor, which sometimes increases further upon storage and/or formulation in cosmetic compositions. This leads to the known products only being able to be used to a limited extent. In cosmetic formulations, it is attempted to conceal this intrinsic odor of the polymers through the use of perfume oils. Apart from the fact that complete concealment of the intrinsic odor is not always possible, the use of perfume oils leads in individual cases to undesired allergic reactions. This limits the use of the known polymers in cosmetic compositions. Moreover, the polymers should per se be less irritative than the products of the prior art and thus suitable for use in antiallergenic cosmetic preparations.

It is an object of the present invention to provide improved polymers based on tert-butyl acrylate and/or tert-butyl methacrylate which, because of their neutral odor, are suitable for a wide use spectrum, in particular in cosmetic compositions, and are also particularly suitable for formulations without the addition of perfume oils. In this connection, it is particularly of interest that the polymers do not develop an intrinsic odor in cosmetic preparations even after storage. In addition, performance properties such as ability to be washed out of the hair, compatibility with other cosmetic ingredients, in particular solubility in water-containing preparations, feel and setting of the treated hair are desired. The provision of polymers which are less irritative than products of the prior art is also desired.

We have found that this object is achieved by acrylate polymers with a K value of from 10 to 60 obtainable by free-radical polymerization of A) 30 to 99% by weight of tert-butyl acrylate and/or tert-butyl methacrylate as monomer A,
B) 1 to 28% by weight of acrylic acid and/or methacrylic acid as monomer B and
C) 0 to 60% by weight of a free-radically copolymerizable monomer or a free-radically copolymerizable monomer mixture as monomer C, where at least one of the monomers C produces a homopolymer with a glass temperature of less than 30° C., with the proviso that the % by weight add up to 100, in the presence of alkanethiols with a carbon chain length of from C 14 to C 22.

We have found that this object is achieved by acrylate polymers with a K value of from 10 to 60, obtainable by free-radical polymerization of A) 30 to 99% by weight of tert-butyl acrylate and/or tert-butyl methacrylate as monomer A,
B) 1 to 28% by weight of acrylic acid and/or methacrylic acid as monomer B and
C) 0 to 60% by weight of a free-radically copolymerizable monomer or a free-radically copolymerizable monomer mixture as monomer C, where at least one of the monomers C produces a homopolymer with a glass transition temperature of less than 30° C., with the proviso that the % by weight add up to 100, in the presence of alkanethiols with a carbon chain length of from C 10 to C 22 and subsequent hydrogen peroxide treatment.

In contrast to products of the prior art, in particular to polymers according to EP 696 916, the polymers obtainable in this way are characterized by freedom from odor and do not develop an odor even during storage either as individual substances or in cosmetic preparations. At the same time, the polymers obtainable in this way exhibit good film-forming properties and good compatibility with customary cosmetic ingredients.

The acrylate polymers are prepared in a known manner by free-radical polymerization of the monomers A, B and optionally C. In this connection, the customary polymerization techniques are used, for example the methods of suspension, emulsion or solution polymerization.

The polymers are prepared in the customary manner using initiators, such as peroxo or azo compounds, for example dibenzoyl oxide, t-butyl perpivalate, t-butyl per-2-ethylhexanoate, di-t-butyl peroxide, t-butyl hydroperoxide, 2,5-dimethyl-2,5-di(t)butylperoxy(hexane), alkali metal or ammonium persulfates, azobisisobutyronitrile, 2,2'-azobis(2-methylbutyronitrile), 2,2'-azobis(2,4-dimethylvaleronitrile), 1,1-azobis(1-cyclohexanecarbonitrile), 2,2'-azobis(2-amidinopropane) salts, 4,4'-azobis(4-cyanovaleric acid) or 2-(carbamoylazo)isobutyronitrile etc., hydrogen peroxide or redox initiators. The initiators are usually used in amounts up to 10% by weight, preferably 0.02 to 5% by weight, based on the monomers to be polymerized.

The emulsion polymerization usually takes place with the exclusion of oxygen at temperatures in the range from 20 to 200° C. The polymerization can be carried out discontinuously or continuously.

Preference is given to metering at least some of the monomers, initiators and alkanethiols simultaneously into the reaction vessel during the polymerization. The monomers, the alkanethiol and the initiator can, however, also be initially introduced into the reactor and polymerized, where in some cases it is necessary to effect cooling.

When the polymerization is complete, an after-polymerization, with the addition of suitable initiators, can be carried out in a known manner to reduce the residual monomer content. If desired, a physical deodorization can also be carried out in the usual manner, for example by introducing water vapor.

The alkanethiols used are linear and branched alkanethiols having a carbon chain length of from C 10 to C 22. Particular preference is given to linear alkanethiols, preference is also given to alkanethiols with a chain length of from C 14 to C 22, in particular from C 14 to C 18. Alkanethiols which may be mentioned are n-decanethiol, n-dodecanethiol, tert-dodecanethiol, n-tetradecanethiol, n-pentadecanethiol, n-hexadecanethiol, n-heptadecanethiol, n-octadecanethiol, n-nonadecanethiol, n-eicosanethiol, n-docosanethiol. Particular preference is given to linear, even-numbered alkanethiols.

The alkanethiols can also be used in mixtures.

The alkanethiols are usually used in amounts of from 0.1 to 5% by weight, in particular 0.25 to 2% by weight, based on the monomers to be polymerized. Usually, the alkanethiols are added to the polymerization together with the monomers.

If alkanethiols with a carbon chain length of from C 10 to C 13 are used, a subsequent hydrogen peroxide treatment is necessary in order to obtain odor-neutral polymers. For this hydrogen peroxide treatment which fires the polymerization, 0.01 to 2.0% by weight, in particular 0.02 to 1.0% by weight, particularly preferably 0.03 to 0.15% by weight, of hydrogen peroxide, in particular 0.1 to 1.0% by weight, based on the monomers to be polymerized, are usually used. It has proven advantageous to carry out the hydrogen peroxide treatment at a temperature of from 20 to 100° C., in particular from 30 to 80° C. The hydrogen peroxide treatment is usually carried out between 30 min and 240 min, in particular between 45 and 90 min.

If alkanethiols with a carbon chain length of from C 14 to C 22 are used, the hydrogen peroxide treatment can be dispensed with. In a further embodiment of the invention, however, it is also possible to follow up with a hydrogen peroxide treatment when alkanethiols having a chain length of from C 14 to C 22 are added.

The polymers should have K values of from 10 to 60, preferably 15 to 50. The K value desired in each case can be set in a manner known per se through the choice of polymerization conditions, for example the polymerization temperature and the initiator concentration. In some instances, particularly when emulsion and suspension polymerization are used, the use of regulators, in particular of sulfur compounds, such as mercaptoethanol, 2-ethylhexyl thioglycolate, thioglycolic acid or dodecylmercaptan, can be used to reduce the K value. The K values are measured in accordance with Fikentscher, Cellulosechemie, Vol. 13, p. 58 to 64 (1932) at 25° C. in 1% strength by weight ethanolic solution and are a measure of the molecular weight.

Such polymers usually have glass transition temperatures between 50 and 130° C., in particular between 60 and 100° C.

If the polymer is prepared by emulsion polymerization, the resulting dispersion can either be incorporated directly into an aqueous, aqueous-alcoholic or alcoholic cosmetic preparation, for example a hair setting preparation, or drying, e.g. spray-drying, of the dispersion can be carried out so that the polymer can be used and processed as a powder.

The polymer obtained in this way can be used directly (not neutralized) in partially or completely neutralized form. In a preferred embodiment, the polymers are partially or completely neutralized.

Neutralization of the polymers usually takes place with an alkali metal hydroxide or preferably with an amine partially or completely, expediently to 5 to 100%, preferably to 30 to 95%. Neutralization preferably takes place with

- a mono-, di- or trialkanolamine having 2 to 5 carbon atoms in the alkanol radical, which may be in etherified form, for example, mono-, di- and triethanolamine, mono-, di- and tri-n-propanolamine, mono-, di- and triisopropanolamine, 2-amino-2-methylpropanol and di(2-methoxyethyl)amine,
- an alkanediolamine having 2 to 5 carbon atoms, for example 2-amino-2-methylpropane-1,3-diol and 2-amino-2-ethylpropane-1,3-diol, or
- a primary, secondary or tertiary alkylamine having a total of 5 to 10 carbon atoms, for example N,N-diethylpropylamine or 3-diethylamino-1-propylamine.

Particularly good results are achieved using 2-amino-2-methylpropanol, triisopropanolamine and 2-amino-2-ethylpropane-1,3-diol and 3-diethylamino-1-propylamine.

Suitable alkali metal hydroxides for the neutralization are primarily sodium hydroxide and potassium hydroxide; also suitable for the neutralization are aqueous buffer solutions, such as, for example, buffers based on alkali metal or ammonium carbonate or bicarbonate. The neutralizing agents are preferably added to the dispersion as dilute aqueous solution.

To modify the properties of the acrylate polymer, at least one further monomer C can also be incorporated by polymerization where necessary. This monomer or at least one of these monomers should produce a homopolymer with a glass transition temperature of less than 30° C. These monomers are preferably chosen from the group consisting of $C_1$–$C_{18}$-alkylacrylates, $C_1$–$C_{18}$-alkylmethacrylates, N—$C_1$–$C_{18}$-alkylacrylamides and N—$C_1$–$C_{18}$-alkylmethacrylamides. Particular preference is given to N—$C_1$–$C_4$-alkylacrylamides or -methacrylamides or mixtures of two or more of these monomers, particular preference being given to unbranched $C_2$—to $C_4$-alkyl acrylates on their own or in a mixture with branched N—$C_3$—to —$C_4$-alkylacrylamides. Suitable $C_1$–$C_4$-alkyl radicals in said (meth)acrylates and (meth)acrylamides are methyl, ethyl, n-propyl, isopropyl, n-butyl, isobutyl, sec-butyl and t-butyl. Particularly preferred monomers B are ethyl acrylate or a mixture of ethyl acrylate and N-t-butylacrylamide.

In a preferred embodiment, the acrylate polymer is obtained from

A) 30 to 72% by weight, in particular 50 to 72% by weight, in particular 60 to 70% by weight, of the monomer A, B) 10 to 28% by weight, in particular 12 to 25% by weight, in particular 15 to 23% by weight, of the monomer B and C) 0 to 60% by weight, in particular 3 to 38% by weight, in particular 7 to 25% by weight, of the monomer C with the proviso that the % by weight add up to 100.

In a further preferred embodiment, the acrylate polymer is made up of

A) tert-butylacrylate as monomer A,

B) methacrylic acid as monomer B and

C) ethyl acrylate or a mixture of ethyl acrylate and N-tert-butylacrylamide as monomer C.

The acrylate polymers according to the invention are characterized by excellent film-forming properties. The invention therefore further provides for the use of the acrylate polymers as film formers.

The acrylate polymers according to the invention are also suitable for use in cosmetic preparations. Suitable here are, in particular, partially or completely neutralized acrylate polymers.

Cosmetic preparations which may be mentioned are skin cosmetic preparations, in particular those for the care and/or cleansing of the skin. These are, in particular, in the form of W/O or O/W skin creams, day and night creams, eye creams, face creams, antiwrinkle creams, moisturizing creams, bleaching creams, vitamin-creams, skin lotions, care lotions and moisturizing lotions. They are also suitable for skin cosmetic preparations, such as face tonics, face masks, deodorants and other cosmetic lotions and for use in decorative cosmetics, for example as concealing stick, stage make-up, in mascara and eyeshadows, lipsticks, kohl pencils, eyeliners, make-up, foundations, blushers and powders and eyebrow pencils.

In addition, the acrylate polymers according to the invention can be used in nose-strips for pore cleansing, in antiacne compositions, repellents, shaving compositions, depilatories, intimate care compositions, footcare compositions and in baby care.

The acrylate polymers can be present in cosmetic preparations as aqueous or aqueous-alcoholic solutions, O/W and W/O emulsions in the form of shampoos, creams, foams, sprays (pumpspray or aerosol), gels, gel sprays, lotions or mousse.

Particular preference is given to the use of the acrylate polymers in hair cosmetic preparations. Hair cosmetic preparations which may be mentioned are hair treatments, hair lotions, hair rinses, hair emulsions, split-end fluids, neutralizing agents for permanent waves, hot-oil treatment preparations, conditioners, curl relaxers, styling wrap lotions, setting lotions, shampoos, hair waxes, pomades, hair foams, hair colorants or hairsprays. Particular preference is given to the use of the acrylate polymers in hairstyle setting compositions which are in the form of spray preparations and/or hair foams.

The acrylate polymers according to the invention are characterized in hair cosmetic preparations by their high compatibility with the nonpolar propellants in spray preparations, in particular with hydrocarbons, such as n-propane, isopropane, n-butane, isobutane, n-pentane and mixtures thereof. They have good hair-setting action and are characterized in that they virtually do not cause the hair to stick together.

In addition to the freedom from odor, the acrylate polymers have excellent results for the performance properties in hair cosmetic preparations. They dissolve in alcohols such as ethanol or isopropanol and in mixtures of these alcohols with water to give clear solutions. The clarity of the solutions is retained even if the solutions are used in standard spray formulations together with propellants such as dimethyl ether. The hair setting compositions according to the invention can be washed out of the hair completely. Hair treated therewith has increased suppleness and a pleasant natural feel. The setting action is simultaneously high here, meaning that in principle it is possible to reduce the required amount of film formers in the hairspray formulation. Due to the freedom from odor of the acrylate polymers, it is possible to dispense with an addition of odor-concealing perfume oils if required. For these reasons, the acrylate polymers are suitable particularly as film formers in hair cosmetic preparations.

The acrylate polymers are usually used in 0.1 to 20% by weight, preferably 0.5 to 10% by weight, in particular 2 to 10% by weight, of the partially or completely neutralized acrylate polymer, based on the cosmetic preparation.

Preference is given to use of the acrylate polymers in cosmetic preparations, in particular in hairspray preparations, which comprise the following constituents:

0.1 to 20% by weight, preferably 0.5 to 10% by weight, in particular 2 to 6% by weight, of the partially or completely neutralized acrylate polymer 1 to 99.9% by weight, preferably 5 to 50% by weight, in particular 10 to 20% by weight, of water 0 to 95% by weight, preferably 20 to 60% by weight, in particular 25 to 50% by weight, of a customary organic solvent, such as primarily ethanol, isopropanol and dimethoxymethane and in addition also acetone, n-propanol, n-butanol, 2-methoxypropan-1-ol, n-pentane, n-hexane, cyclohexane, n-heptane, n-octane or dichloromethane or mixtures thereof 0 to 90% by weight, preferably 30 to 80% by weight, in particular 45 to 60% by weight, of a customary propellant, such as n-propane, isopropane, n-butane, isobutane, 2,2-dimethylbutane, n-pentane, isopentane, dimethyl ether, difluoroethane, fluorotrichloromethane, dichlorodifluoromethane or dichlorotetrafluoroethane, HCF 152 A or mixtures thereof Of the compounds given, the propellants (propellant gases) used are primarily the hydrocarbons, in particular propane, n-butane, n-pentane and mixtures thereof, and also dimethyl ether and difluoroethane. Where appropriate, one or more of said chlorinated hydrocarbons are co-used in propellant mixtures, but only in small amounts, for example up to 20% by weight, based on the propellant mixture.

The hair cosmetic preparations according to the invention are also particularly suitable for pump spray preparations without the addition of propellants, or else for aerosol sprays with customary compressed gases, such as nitrogen, compressed air or carbon dioxide as propellant.

A water-containing standard spray formulation has, for example, the following composition:

| | |
|---|---|
| 2 to 10% by weight | of the acrylate polymer neutralized to 100% with 2-amino-2-methylpropanol |
| 10 to 76% by weight | of ethanol |
| 2 to 20% by weight | of water |
| 10 to 60% by weight | of dimethyl ether and/or propane/n-butane and/or propane/isobutane. |

For the targeted setting of properties of hair cosmetic preparations, it may be advantageous to use the acrylate polymers according to the invention as a mixture with further hair setting polymers.

Suitable hair cosmetics polymers are, for example, anionic polymers. Such anionic polymers are homo- and copolymers of acrylic acid and methacrylic acid different from the acrylate polymers according to the invention, or salts thereof, copolymers of acrylic acid and acrylamide and salts thereof; sodium salts of polyhydroxycarboxylic acids, water-soluble or water-dispersible polyesters, polyurethanes (e.g. Luviset P.U.R) and polyureas. Particularly suitable polymers are copolymers of ethyl acrylate and methacrylic acid (e.g. Luvimer®MAE), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohols, anionic polysiloxanes, e.g. carboxyfunctional copolymers of vinylpyrrolidone, t-butyl acrylate, methacrylic acid (e.g. Luviskol® VBM) or terpolymers of tert-butyl acrylate, methacrylic acid and dimethicone copolyol (e.g. Luviflex® Silk).

Further suitable hair cosmetic polymers are also neutral polymers, such as polyvinylpyrrolidones, copolymers of N-vinylpyrrolidone and vinyl acetate and/or vinyl propionate, polysiloxanes, polyvinylcaprolactam and copolymers containing N-vinylpyrrolidone, cellulose derivatives, polyaspartic acid salts and derivatives.

The acrylate polymers can be formulated in cosmetic preparations using customary further auxiliaries. Further customary auxiliaries which may be mentioned are: surfactants, oily bodies, emulsifiers, coemulsifiers, superfatting agents, pearlescent waxes, bodying agents, thickeners, fats, waxes, silicone compounds, hydrotrophic agents, preservatives, perfume oils, dyes, stabilizers, pH regulators, care substances, such as panthenol, phytantriol, collagen, vitamins and proteinaceous substances, solubilizers, glitter substances, complexing agents and the like.

Suitable anionic surfactants are, for example, alkyl sulfates, alkyl ether sulfates, alkylsulfonates, alkylarylsulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

Suitable compounds are, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkyl amphoacetates or amphopropionates, alkyl amphodiacetates or amphodipropionates.

For example, cocodimethylsulfopropylbetaine, laurylbetaine, cocamidopropylbetaine or sodium cocamphopropionate may be used.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is approximately 6 to 60 mol per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

In addition, the compositions can comprise customary cationic surfactants, such as e.g. quaternary ammonium compounds, for example cetyltrimethylammonium chloride.

If the acrylate polymers according to the invention are used in shampoo formulations, they usually comprise anionic surfactants as base surfactants, and amphoteric and nonionic surfactants as cosurfactants.

The cosmetic preparations usually comprise 2 to 50% by weight of surfactants, preferably 5 to 40% by weight, particularly preferably 8 to 30% by weight.

Suitable oil bodies are, for example, Guerbet alcohols based on fatty alcohols having 6 to 18, preferably 8 to 10, carbon atoms, esters of linear $C_6$–$C_{22}$-fatty acids with linear $C_6$–$C_{22}$-fatty alcohols, esters of branched $C_6$–$C_{13}$-carboxylic acids with linear $C_6$–$C_{22}$-fatty alcohols, esters of linear $C_6$–$C_{22}$-fatty acids with branched alcohols, in particular 2-ethylhexanol, esters of hydroxycarboxylic acids with linear or branched $C_6$–$C_{22}$-fatty alcohols, in particular dioctyl malate, esters of linear and/or branched fatty acids with polyhydric alcohols (such as e.g. propylene glycol, dimerdiol or trimertriol) and/or Guerbet alcohols, triglycerides based on $C_6$–$C_{10}$-fatty acids, liquid mono-/di-/triglyceride mixtures based on $C_6$–$C_{18}$-fatty acids, esters of $C_6$–$C_{22}$-fatty alcohols and/or Guerbet alcohols with aromatic carboxylic acids, in particular benzoic acid, vegetable oils, branched primary alcohols, substituted cyclohexanes, linear and branched $C_6$–$C_{22}$-fatty alcohol carbonates, Guerbet carbonates, esters of benzoic acid with linear and/or branched $C_6$–$C_{22}$-alcohols (e.g. Finsolv® TN), linear or branched, symmetrical or unsymmetrical dialkyl ethers having 6 to 22 carbon atoms per alkyl group, ring-opening products of epoxidized fatty acid esters with polyols, silicone oils and/or aliphatic or naphthenic hydrocarbons.

Suitable emulsifiers are, for example, nonionogenic surfactants from at least one of the following groups:

(1) addition products of 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group;

(2) $C_{12/18}$-fatty acid mono- and diesters of addition products of from 1 to 30 mol of ethylene oxide onto glycerol;

(3) glycerol mono- and diesters and sorbitan mono- and diesters of saturated and unsaturated fatty acids having 6 to 22 carbon atoms and the ethylene oxide addition products thereof;

(4) alkyl mono- and oligoglycosides having 8 to 22 carbon atoms in the alkyl radical and the ethoxylated analogs thereof;

(5) addition products of from 15 to 60 mol of ethylene oxide onto castor oil and/or hydrogenated castor oil;

(6) polyol and, in particular, polyglycerol esters, such as e.g. polyglycerol polyricinoleate, polyglycerol poly- 12-hydroxystearate or polyglycerol dimerate. Also suitable are mixtures of compounds of two or more of these classes of substance;
(7) addition products of from 2 to 15 mol of ethylene oxide onto castor oil and/or hydrogenated castor oil;
(8) partial esters based on linear, branched, unsaturated or saturated $C_{6/22}$-fatty acids, ricinoleic acid, and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside), and polyglucosides (e.g. cellulose);
(9) mono-, di- and trialkyl phosphate, and mono-, di- and/or tri- PEG alkyl phosphates and salts thereof;
(10) wool wax alcohols;
(11) polysiloxane-polyalkyl-polyether copolymers or corresponding derivatives;
(12) mixed esters of pentaerythritol, fatty acids, citric acid and fatty alcohol according to German patent 1165574 and/or mixed esters of fatty acids having 6 to 22 carbon atoms, methylglycose and polyols, preferably glycerol or polyglycerol, and
(13) polyalkylene glycols.

The addition products of ethylene oxide and/or propylene oxide onto fatty alcohols, fatty acids, alkylphenols, glycerol mono- and diesters, and sorbitan mono- and diesters of fatty acids or with castor oil are known, commercially available products. They are homolog mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide onto glycerol are known from German patent 2024051 as refatting agents for cosmetic preparations. $C_{8/18}$-alkyl mono- and oligoglycosides, their preparation and their use are known from the prior art. Their preparation takes place, in particular, by reacting glucose or oligosaccharides with primary alcohols having 8 to 18 carbon atoms. With regard to the glycoside ester, monoglycosides in which a cyclic sugar radical is bonded to the fatty alcohol glycosidically, and also oligomeric glycosides having a degree of oligomerization up to preferably about 8 are suitable. The degree of oligomerization here is a statistical average value which is based on a homolog distribution customary for such technical-grade products.

It is also possible for the emulsifiers. used to be zwitterionic surfactants. Zwitterionic surfactants is the term used to refer to those surface-active compounds which carry at least one quaternary ammonium group and at least one carboxylate and one sulfonate group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethyl hydroxyethylcarboxymethylglycinate. Particular preference is given to the fatty acid amide derivative known under the CTFA name Cocamidopropyl Betaine. Likewise suitable emulsifiers are ampholytic surfactants. Ampholytic surfactants are understood as meaning those surface-active compounds which, apart from a $C_{8/18}$-alkyl or acyl group in the molecule, contain at least one free amino group and at least one —COOH— or —SO$_3$H— group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocacylaminoethylaminopropionate and $C_{12/18}$-acylsarcosine. In addition to the ampholytic emulsifiers, quaternary emulsifiers are also suitable, those of the esterquat type, preferably methylquaternized difatty acid triethanolamine ester salts, being particularly preferred.

As superfatting agents, it is possible to use substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Examples of suitable pearlescent waxes are: alkylene glycol esters, specifically ethylene glycol disterate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Suitable bodying agents are primarily fatty alcohols or hydroxy fatty alcohols having 12 to 22 and, preferably, 16 to 18 carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, polysaccharides, in particular xanthan gum, guar guar, agar agar, alginates and Tyloses, carboxymethylcellulose and hydroxyethylcellulose, and also relatively high molecular weight polyethylene glycol mono- and diesters of fatty acids, polyacrylates (e.g. Carbopols® from Goodrich or Synthalense® from Sigma), polyacrylamides, polyvinyl alcohol and polyvinylpyrrolidone, surfactants, such as, for example, ethoxylated fatty acid glycerides, esters of fatty acids with polyols, such as, for example, pentaerythritol or trimethylolpropane, fatty alcohol ethoxylates having a narrowed homolog distribution or alkyl oligoglucosides, and electrolytes, such as sodium chloride and ammonium chloride.

Typical examples of fats are glycerides, and suitable waxes are, inter alia, beeswax, carnauba wax, candelilla wax, montan wax, paraffin wax or microcrystalline waxes, optionally in combination with hydrophilic waxes, e.g. cetylstearyl alcohol or partial glycerides. Stabilizers which may be used are metal salts of fatty acids, such as e.g. magnesium, calcium, aluminum and/or zinc stearate or ricinoleate.

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be in liquid or resin form at room temperature.

To improve the flow behavior, it is also possible to use hydrotropic agents, such as, for example, ethanol, isopropyl alcohol or polyols. Polyols which are suitable here preferably have 2 to 15 carbon atoms and at least two hydroxyl groups.

Typical examples are
glycerol;
alkylene glycols, such as, for example, ethylene glycol, diethylene glycol, propylene glycol, butylene glycol, hexylene glycol, and polyethylene glycols having an average molecular weight of from 100 to 1000 daltons;
technical-grade oligoglycerol mixtures having a degree of self-condensation of from 1.5 to 10, such as, for example, technical-grade diglycerol mixtures with a diglycerol content of from 40 to 50% by weight;
methylol compounds, such as, in particular, trimethylolethane, trimethylolpropane, trimethylolbutane, pentaerythritol and dipentaerythritol;
lower alkylglucosides, in particular those having 1 to 8 carbon atoms in the alkyl radical, such as, for example, methyl and butyl glucoside;
sugar alcohols having 5 to 12 carbon atoms, such as, for example, sorbitol or mannitol;
sugars having 5 to 12 carbon atoms, such as, for example, glucose or sucrose;
amino sugars, such as, for example, glucamine.

Examples of suitable preservatives are phenoxyethanol, formaldehyde solution, parabens, pentanediol or sorbic acid, and the other classes of substance listed in Appendix 6, Part A and B, of the Cosmetics Directive.

The addition of perfume oils to conceal the odor of the polymers is not necessary. In some cases, the cosmetic preparations may nevertheless comprise perfume oils. Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycidate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonal, and the ketones include, for example, the ionones, α-isomethylionone and methyl cedryl ketone, and the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing scent note. Essential oils of lower volatility, which are mostly used as flavor components, are also suitable as perfume oils, e.g. sage oil, camomile oil, oil of cloves, balm oil, mint oil, cinnamon leaf oil, lime blossom oil, juniperberry oil, vetiver oil, olibanum oil, galbanum oil, labdanum oil and lavandin oil.

Preference is given to using bergamot oil, dihydromyrcenol, lilial, lyral, citronellol, phenylethyl alcohol, α-hexylcinnamaldehyde, geraniol, benzylacetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, Romillat, Irotyl and Floramat alone or in mixtures.

Dyes which may be used are the substances approved and suitable for cosmetic purposes, as are listed, for example, in the publication "Kosmetische Färbemittel" [Cosmetic Colorants] from the Farbstoffkommission der Deutschen Forschungsgemeinschaft [Dyes Commission of the German Research Council], Verlag Chemie, Weinheim, 1984, pp. 81–106. These dyes are usually used in concentrations of from 0.001 to 0.1% by weight, based on the total mixture.

Further suitable polymers are, for example, cationic polymers with the INCI designation Polyquaternium, such as, for example, copolymers of N-vinylpyrrolidone/N-vinylimidazolium salts (Luviquat®FC, Luviquat ®HM, Luviquat® MS, Luviquat Care®), copolymers of N-vinylcaprolactam/N-vinylpyrrolidone/N-vinylimidazolium salts (Luviquat Hold®), copolymers of N-vinylpyrrolidone/dimethylaminoethyl methacrylate, quaternized with diethyl sulfate (Luviquat® PQ11), cationic cellulose derivatives (Polyquaternium-4 and -10), acrylamide copolymers (Polyquaternium-7) and guar hydroxypropyltrimethylammonium chloride (INCI: Hydroxypropyl Guar Hydroxypropyltrimonium Chloride). Suitable polymers are also polyethyleneimines and salts thereof, polyvinylamines and salts thereof.

The total content of the auxiliaries and additives can be 1 to 50% by weight, preferably 5 to 40% by weight, based on the composition.

The present invention further provides a process for the preparation of acrylate polymers in which alkanethiols, in particular linear alkanethiols with a carbon chain length of from C 14 to C 22 are used. The alkanethiols are usually used here together with the monomers to be polymerized.

The alkanethiols are used here usually in amounts of from 0.1 to 5% by weight, based on the monomers to be polymerized.

The present invention further provides a process for the preparation of acrylate polymers in which alkanethiols, in particular linear alkanethiols with a carbon chain length of from C 10 to C 22, are used and, when the polymerization is complete, a hydrogen peroxide treatment is carried out.

The acrylate polymers obtainable by the process according to the invention are characterized by low to no intrinsic odor.

The processes according to the invention are generally suitable for the preparation of acrylate polymers, in particular those described in claims 1 and 2.

Moreover, the processes according to the invention are suitable for the preparation of further acrylate polymers.

Suitable acrylate polymers are all polymers which contain at least one monomer based on acrylate.

Representative but nonlimiting examples of suitable monomers are, for example, acrylic acid and salts, esters and amides thereof. The salts can be derived from any desired nontoxic metal, ammonium or substituted ammonium counterion.

The esters can be derived from $C_1$–$C_{40}$ linear, $C_3$–$C_{40}$ branched-chain, or $C_3$–$C_{40}$ carbocyclic alcohols, from polyfunctional alcohols having 2 to about 8 hydroxyl groups, such as ethylene glycol, hexylene glycol, glycerol, and 1,2,6-hexanetriol, from aminoalcohols or from alcohol ethers, such as methoxyethanol and ethoxyethanol or polyethylene glycols.

Also suitable are N,N-dialkylaminoalkyl acrylates and methacrylates and N-dialkylaminoalkylacrylamides and -methacrylamides of the formula (I)

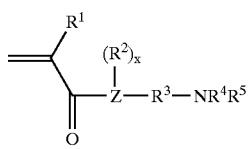

where $R^1$=H, alkyl having 1 to 8 carbon atoms,
$R^2$=H, methyl,
$R^3$=alkylene having 1 to 24 carbon atoms, optionally substituted by alkyl,
$R^4$, $R^5$=$C_1$–$C_{40}$ alkyl radical,
Z=nitrogen when x=1 or oxygen when x=0

The amides can be unsubstituted, N-alkyl or N-alkylamino-monosubstituted, or N,N-dialkyl-substituted or N,N-dialkylamino-disubstituted, in which the alkyl or alkylamino groups are derived from C1–C40 linear, C3–C40 branched-chain or C3–C40 carbocyclic units. Additionally, the alkylamino groups may be quarternized.

Preferred monomers of the formula I are N,N-dimethylaminomethyl (meth)acrylate, N,N-diethylaminomethyl (meth)acrylate, N,N-dimethylaminoethyl (meth)acrylate, N,N-diethylaminoethyl (meth)acrylate.

Monomers which can likewise be used are substituted acrylic acids and salts, esters and amides thereof, where the substituents on the carbon atoms are in the two or three position of the acrylic acid, and, independently thereof, are chosen from the group consisting of C1–C4 alkyl, —CN, COOH, particularly preferably methacrylic acid, ethacrylic acid and 3-cyanoacrylic acid. These salts, esters and amides of the substituted acrylic acids can be chosen as described above for the salts, esters and amides of acrylic acid.

Particularly suitable monomers are acrylic acid, methacrylic acid, ethylacrylic acid, methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate isobutyl methacrylate, t-butyl methacrylate, 2-ethylhexyl methacrylate, decyl methacrylate, methyl ethacrylate, ethyl ethacrylate, n-butyl ethacrylat, isobutyl ethacrylate, t-butyl ethacrylate, 2-ethylhexyl ethacrylate, decyl ethacrylate, 2,3-dihydroxypropyl acrylate, 2,3-dihydroxypropyl methacrylate, 2-hydroxyethyl acrylate, hydroxypropyl acrylates, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate,hydroxypropyl methacrylates, glyceryl monoacrylate, glyceryl monomethacrylate, polyalkylene glycol (meth)acrylates, unsaturated sulfonic acids, such as, for example, acrylamidopropane sulfonic acid;

acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, 1-vinylimidazole, 1-vinyl-2-methylimidazole, N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl]methacrylamide, N-[3-(diethylamino)propyl]methacrylamide, N-[3-(diethylamino)propyl]acrylamide;

of these, particular preference is given to acrylic acid, methacrylic acid, methyl acrylate, methyl methacrylate, ethyl acrylate, ethyl methacrylate, n-butyl-acrylate, n-butyl methacrylate, t-butyl acrylate, t-butyl methacrylate, isobutyl acrylate, isobutyl methacrylate, 2-ethylhexyl acrylate, N-t-butylacrylamide, N-octylacrylamide, 2-hydroxyethyl acrylate, hydroxypropyl acrylate, 2-hydroxyethyl methacrylate, hydroxypropyl methacrylate, alkylene glycol (meth)acrylates, unsaturated sulfonic acids, such as, for example, acrylamidopropanesulfonic acid or diethyl sulfate.

The processes according to the invention are suitable in particular for the preparation of homo- and copolymers of acrylic acid and acrylamide and salts thereof, copolymers of tert-butyl acrylate, ethyl acrylate, methacrylic acid, (e.g. Luvimer® 100 P), copolymers of ethyl acrylate and methacrylic acid (e.g. Luviflex® Soft), copolymers of N-tert-butylacrylamide, ethyl acrylate, acrylic acid (Ultrahold Strong®), copolymers of acrylic acid and methacrylic acid with hydrophobic monomers, e.g. $C_4$–$C_{30}$-alkyl esters of (meth)acrylic acid, $C_4$–$C_{30}$-alkyl vinyl esters, $C_4$–$C_{30}$-alkyl vinyl ethers and hyaluronic acid and further polymers known under the trade names Amerhold DR-25, Ultrahold®, Acronal®, Acudyne®, Lovocryl®, Versatyl®, Amphomer® (28-4910, LV-71), Placise® L53, Advantage Plus®, Balance® (0/55), Acudyne® 255.

The list below is the INCI/CTFA names and the manufacturers of the acrylate polymers for which the processes according to the invention are suitable:

| INCI/CTFA | Polymer | Manufacturer |
|---|---|---|
| Acrylates Copolymer | Amerhold DR-25 | Amerchol |
| Styrene/Acrylates Copolymer | Acronal 290 D, 296 D | BASF |
| Acrylates/Acrylamide Copolymer | Ultrahold 8 | BASF |
| Acrylates/Acrylamide Copolymer | Ultrahold Strong | BASF |
| Acrylates Copolymer | Luviflex Soft | BASF |
| Acrylates Copolymer | Luvimer 100 P, 36 D, 30 E | BASF |
| Methacryloyl Ethylbetaine/Acrylates Copolymer | Diaformer | Clariant |
| Acrylates/Diacetoneacrylamide Copolymer | Placsize L-53 | Goo Chemical |
| Vinyl Caprolactain/PVP/ Dimethylaminoethyl Methacrylate Copolymer | Copolymer VC 713 (= Advantage HC) | ISP |
| Vinyl Caprolactam/ PVP/Dimethylaminoethyl Methacrylat Copolymer | H$_2$OLD ® EP-1 | ISP |
| VA/Butyl Maleate/Isobornyl Acrylate | Advantage Plus | ISP |
| PVP/DMAPA Acrylates Copolymer | Styleeze CC-10 | ISP |
| PVP/Vinylcaprolactam/DMAPA Acrylates Copolymer | Aquaflex SF-40 | ISP |
| Octylacrylamide/Acrylates/ Butylaminoethyl Methacrylate Copolymer | Amphomer 28-4910 | National Starch |
| Octylacrylamide/Acrylates/ Butylaminoethyl Methacrylate Copolymer | Amphomer LV-71 | National Starch |
| Acrylates/Octylacrylamide Copolymer | Versatyl 42 | National Starch |
| Octylacrylamide/Acrylates Copolymer | Versatyl 90 | National Starch |
| Acrylates Copolymer | Balance 0/55 | National Starch |
| Octylacrylamide/Acrylates/Butyl aminoethyl Methacrylate Copolymer | Lovocryl 47 | National Starch |
| Acrylates/Hydroxyesters Acrylates | Acudyne | Robin & Haas |

The polymerization processes can be carried out as solution polymerization, emulsion polymerization, inverse emulsion polymerization, suspension polymerization, inverse suspension polymerization or precipitation polymerization, without the methods which can be used being limited thereto. In solution polymerization, water or customary organic solvents can be used as solvent.

EXAMPLES

Example 1

Preparation of an Acrylate Polymer E 5 (Emulsion Polymerization)

An emulsion was prepared from 2.5 g of sodium lauryl sulfate, 15.6 g of a standard commercial nonionic emulsifier, 300 g of water, 140 g of methacrylic acid (monomer B), 490 g of tert-butyl acrylate (monomer A), 70 g ethyl acrylate (monomer C) and 3 g of tert-dodecylmercaptan. This emulsion was metered into a polymerization vessel which contained 750 g of water in a feed method over the course of a polymerization time of about 2 to 4 hours at about 75 to 85° C. The polymerization initiator, 1.1 g of sodium persulfate dissolved in 14.9 g of water, was added when the emulsion feed was started. When the polymerization was complete, 3.6 g of hydrogen peroxide (50% strength) were metered in at 60 to 70° C.

The preparation of the other examples (E1 to E4 and E6 to E9) and of the comparative examples C1 (in accordance with EP 696 916) to C5 was carried out in accordance with Example 1. The corresponding amounts of monomers A, B and C and the type and amount of alkanethiol and, where appropriate, hydrogen peroxide are given in the table below.

The odor assessment of the acrylate polymers prepared was carried out by a panel of 4 test persons. For this, the acrylate polymers prepared according to the examples were dried, dissolved 30% in ethanol and then formulated as 3% strength aqueous solution and 100% neutralized with 2-amino-2-methylpropanol. Evaluation of the odor properties is in accordance with the following classification:

"1" no odor

"2", weak, unpleasant odor

"3" strong, unpleasant odor

| Ex. No. | Composition [% by wt.] | | | | Addition | Amount of Addition [% by wt.] | H$_2$O$_2$ [% by wt.] | Odor |
|---|---|---|---|---|---|---|---|---|
| | t-BA | MAA | EA | t-BAA | | | | |
| C 1 | 70 | 18 | 12 | — | Mercaptoethanol | 0.3 | — | 2 |
| C 2 | 72 | 18 | 10 | — | n-Butanethiol | 0.15 | — | 3 |
| C 3 | 72 | 18 | 10 | — | n-Butanethiol | 0.15 | 0.40 | 3 |
| C 4 | 65 | 15 | 20 | — | 1-Octanethiol | 0.45 | 0.50 | 3 |
| E 1 | 65 | 15 | 20 | — | Decanethiol | 0.50 | 0.30 | 1 |
| E 2 | 65 | 20 | 5 | 10 | Decanethiol | 0.50 | 0.40 | 1 |
| E 3 | 65 | 15 | 20 | — | Decanethiol | 0.50 | 0.50 | 1 |
| C 5 | 65 | 15 | 10 | 10 | n-Dodecanethiol | 0.45 | — | 2 |
| C 6 | 70 | 20 | 10 | — | tert-Dodecanethiol | 0.40 | — | 2 |

-continued

| Ex. No. | Composition [% by wt.] | | | | Addition | Amount of Addition [% by wt.] | $H_2O_2$ [% by wt.] | Odor |
|---|---|---|---|---|---|---|---|---|
| | t-BA | MAA | EA | t-BAA | | | | |
| E 4 | 65 | 15 | 10 | 10 | n-Dodecanethiol | 0.45 | 0.30 | 1 |
| E 5 | 70 | 20 | 10 | — | n-Dodecanethiol | 0.40 | 0.25 | 1 |
| E 6 | 67 | 23 | 10 | — | n-Dodecanethiol | 0.43 | 0.50 | 1 |
| E 7 | 67 | 23 | 10 | — | n-Dodecanethiol | 0.4 | 0.11 | 1 |
| E 8 | 50 | 20 | 20 | 10 | n-Dodecanethiol | 0.35 | 0.40 | 1 |
| E 9 | 67 | 23 | 10 | — | n-Octadecanethiol | 0.50 | 0.20 | 1 |
| E 10 | 60 | 20 | 20 | — | n-Octadecanethiol | 0.50 | 0.50 | 1 |

Explanations to the table
t-BA = tert-butyl acrylate
MAA = methacrylic acid
AA = acrylic acid
EA = ethyl acrylate
t-BAA = N-tert-butyl acrylamide Formulation Examples

| Ingredient | INCI | Formulation 1 Aerosol Hairspray | Formulation 2 Aerosol Hairspray | Formulation 3 Aerosol Hairspray | Formulation 4 Pump-spray |
|---|---|---|---|---|---|
| | | Data in % by wt. | | | |
| Acrylate polymer as in Example 1, 100% neutralized with AMP | Acrylate Copolymer | 4.0 | 2.0 | 4.0 | 5.0 |
| 2-Amino-2-methylpropanol (AMP) | Aminomethyl Propanol | 0.95 | 0.47 | 0.93 | 1.18 |
| Water | Water | — | — | 7.15 | 13.82 |
| Dow Corning 190 Polyether or Wacker DMC 6031 | Dimethicone Copolyole | 0.1 | | 0.01 | |
| Luvitol EHO | Cetearyl Octanoate | 0.1 | | | |
| Dow Corning 344 fluid or Wacker CM 040 | Cyclomethicone | | | 0.05 | |
| D-Panthenol USP | Panthenol | | | 0.1 | |
| Abil B 8843 or Wacker DMC 6032 | Dimethicone Copolyole | | | 0.1 | |
| Ethanol abs. | Alcohol | 54.75 | 47.23 | | 80.00 |
| Ethanol 96% | Alcohol | | | 42.77 | |
| Propane/Butane | Propane/Butane | 40.0 | 50.0 | | |
| Dimethyl Ether | Dimethyl Ether | | | 45.0 | |

We claim:

1. An acrylate polymer with a K value of from 10 to 60, obtained by free-radical polymerization of 30 to 99% by weight of tert-butyl acrylate and/or tert-butyl methacrylate as monomer A, 1 to 28% by weight of acrylic acid and/or methacrylic acid as monomer B and 0 to 60% by weight of a free-radically copolymerizable monomer or a free-radically copolymerizable monomer mixture as monomer C, where at least one of the monomers C produces a homopolymer with a glass transition temperature of less than 30° C., with the proviso that the % by weight add up to 100, in the presence of alkanethiols with a carbon chain length of from C 10 to C 22 and subsequent hydrogen peroxide treatment.

and subsequent hydrogen peroxide treatment.

2. An acrylate polymer as claimed in claim 1, wherein linear alkanethiols are used.

3. An acrylate polymer as claimed in claim 1, wherein 0.1 to 5% by weight of alkanethiols, based on the monomers to be polymerized, are used.

4. An acrylate polymer as claimed in claim 1, wherein the monomer C is chosen from the group formed by $C_1$- to $C_{18}$-alkyl acrylate, $C_1$- to $C_{18}$-methacrylate, N—$C_1$- to —$C_{18}$-alkylacrylamides and N—$C_1$- to $C_{18}$-methacrylamides.

5. An acrylate polymer as claimed in claim 1, wherein

A) 30 to 72% by weight of the monomer A,

B) 10 to 28% by weight of the monomer B and

C) 0 to 60% by weight of the monomer C are used, with the proviso that the % by weight add up to 100.

6. An acrylate polymer as claimed in claim 1, wherein

A) tert-butyl acrylate is used as monomer A

B) methacrylic acid is used as monomer B

C) ethyl acrylate or a mixture of ethyl acrylate and N-tert-butylacrylamide is used as monomer C.

7. A film former comprising an acrylate polymer as claimed in claim 1.

8. A cosmetic preparation comprising an acrylate polymer as claimed claim 1.

9. The cosmetic preparation as claimed in claim 8 in hair cosmetic preparations.

10. A process for the preparation of acrylate polymers, which comprises carrying out the polymerization in the presence of alkanethiols with a carbon chain length of from C 14 to C 22.

11. A process for the preparation of acrylate polymers, which comprises a) carrying out the polymerization in the presence of alkanethiols with a carbon chain length of from C 10 to C 22 and then
b) carrying out a treatment with hydrogen peroxide.

12. A process as claimed in claim 10, wherein 0.1 to 5% by weight of alkanethiol, based on the amount of monomers to be polymerized, is used.

13. A process as claimed in claim 11, wherein the treatment is carried out with 0.01 to 2% by weight of hydrogen peroxide, based on the amount of monomers to be polymerzied.

14. An acrylate polymer made from an alkanethiol with a carbon chain length of from C 14 to C 22.

* * * * *